(12) United States Patent
Alexander (10) Patent No.: US 10,213,281 B2
(45) Date of Patent: Feb. 26, 2019

(54) NON-SURGICAL SYSTEMS AND METHODS FOR TREATING RECEDING GUMS

(71) Applicant: Eric Jay Alexander, Orem, UT (US)

(72) Inventor: Eric Jay Alexander, Orem, UT (US)

(*) Notice: Subject to any disclaimer, the term of this patent is extended or adjusted under 35 U.S.C. 154(b) by 582 days.

(21) Appl. No.: 14/789,812

(22) Filed: Jul. 1, 2015

(65) Prior Publication Data

US 2016/0000544 A1  Jan. 7, 2016

Related U.S. Application Data (60) Provisional application No. 62/034,261, filed on Aug. 7, 2014, provisional application No. 62/019,883, filed on Jul. 1, 2014.

(51) Int. Cl.
| | | |
|---|---|---|
| A61C 19/06 | (2006.01) | |
| A61H 9/00 | (2006.01) | |
| A61H 13/00 | (2006.01) | |
| A61C 9/00 | (2006.01) | |
| A61C 13/34 | (2006.01) | |

(52) U.S. Cl.
CPC ............ *A61C 19/06* (2013.01); *A61C 19/063* (2013.01); *A61H 9/0057* (2013.01); *A61H 13/00* (2013.01); *A61C 9/0006* (2013.01); *A61C 13/34* (2013.01); *A61H 2201/1647* (2013.01)

(58) Field of Classification Search
CPC ....... A61C 9/00; A61C 9/0006–9/0013; A61C 9/0026; A61C 17/02; A61C 17/0208; A61C 17/0211; A61C 17/022; A61C 17/04–17/046; A61C 19/06; A61C 19/063; A61C 13/34; A61H 13/00; A61H 9/0057; A61H 2201/1647

USPC ........................................................ 433/214
See application file for complete search history.

(56) References Cited

U.S. PATENT DOCUMENTS

| | | | | |
|---|---|---|---|---|
| 4,583,949 A * | 4/1986 | Heartness | ............... | A61C 13/25 433/185 |
| 5,129,824 A * | 7/1992 | Keller | ..................... | A61C 15/00 433/215 |
| 5,365,624 A * | 11/1994 | Berns | .................. | A61C 17/0211 15/22.1 |
| 6,394,802 B1 * | 5/2002 | Hahn | .................... | A61C 9/0006 433/37 |
| 2005/0221254 A1 * | 10/2005 | Kohani | ................ | A61C 9/0006 433/37 |
| 2006/0068364 A1 | 3/2006 | Struck | | |

(Continued)

*Primary Examiner* — Joshua Lee
(74) *Attorney, Agent, or Firm* — Kirton McConkie; Adam D. Stevens (57) ABSTRACT

A non-surgical treatment for receding gums utilizes the fact that tissue responds to continuous controlled mechanical forces with growth. The treatment system includes an impression of the upper and/or lower teeth, including the surrounding existing gums, so that a vacuum can be established within the impression around teeth and gums. Before use, selected portions of the impression are carved out a desired amount to create a location for the expansion and regrowth of the gums. Additionally, one or more channels may be included in the impression for delivery of the vacuum to all areas encompassed by the impression. The treatment system also includes a vacuum source operatively attached to the impression so as to be able to deliver a vacuum to the impression once the impression is place in the patient's mouth over the teeth and gums.

6 Claims, 7 Drawing Sheets

(56) References Cited

U.S. PATENT DOCUMENTS

| | | | |
|---|---|---|---|
| 2007/0054237 A1* | 3/2007 | Neuschafer | A61C 9/0006 |
| | | | 433/37 |
| 2007/0054243 A1 | 3/2007 | Schemmer et al. | |
| 2008/0066768 A1 | 3/2008 | Dembro | |
| 2009/0208896 A1 | 8/2009 | Clark | |
| 2009/0220601 A1 | 9/2009 | Cutler | |
| 2012/0156640 A1* | 6/2012 | Keller | A61C 19/063 |
| | | | 433/80 |
| 2014/0199653 A1* | 7/2014 | Kurthy | A61C 9/0006 |
| | | | 433/40 |
| 2014/0271499 A1* | 9/2014 | Keller | A61K 6/007 |
| | | | 424/53 |

\* cited by examiner

NON-SURGICAL SYSTEMS AND METHODS FOR TREATING RECEDING GUMS

CROSS-REFERENCE TO RELATED APPLICATIONS

This application claims the benefit of U.S. Provisional Patent Application No. 62/019,883, filed Jul. 1, 2014 and U.S. Provisional Patent Application No. 62/034,261, filed Aug. 7, 2014.

BACKGROUND OF THE INVENTION

1. Field of the Invention

The present invention relates to treatment of receding gums, and more particularly to non-surgical methods for treating receding gums.

2. Background and Related Art

In dentistry, gingival recession (receding gums) is the exposure in the roots of the teeth caused by a loss of gum tissue and/or retraction of the gingival margin from the crown of the teeth. Gum recession is a common problem in adults over the age of 40, but it may also occur starting from the teens. It may exist with or without concomitant decrease in crown-to-root ratio (recession of alveolar bone).

Depending on the shape of the gum recession and the levels of bone around the teeth, areas of gum recession can be regenerated with new gum tissue using a variety of gum grafting "periodontal plastic surgery" procedures performed by a specialist in periodontics (a periodontist). These procedures are typically completed under local anesthesia with or without conscious sedation, as the patient prefers. This may involve repositioning of adjacent gum tissue to cover the recession (called a pedicle graft), or use of a free graft of gingival or connective tissue from the roof of the mouth (called a free gingival graft or a subepithelial connective tissue graft). Alternatively, a material called acellular dermal matrix (processed donated human skin allograft) may be used instead of tissue from the patient's own palate.

Recent advances have seen the introduction of platelet derived growth factor (PDGF) infused bone graft material. This material is usually combined with the cellular matrix to form a soft bone paste that is then covered by the allograft. The development of this type of bone and tissue cellular matrix (also known as ortho filler), results in greater osseointegration with the patient's healthy bone and soft tissue. Healing from such procedures requires 2-4 weeks. After a few months the results can be evaluated and in some cases the new tissue needs to be reshaped in a very minor procedure to get an optimal result.

Many such procedures are painful and many also require significant time before a second procedure can be done, such as on additional areas. When tissue is harvested from the roof of the mouth, the roof of the mouth can be sore for a number of weeks. Additionally, a restrictive diet is sometimes required to aid in healing. Finally, time is required for connective tissue regrowth before a second tissue harvest can occur.

Recently, a less-invasive treatment for gum recession has been developed called the "Chao Pinhole Surgical Technique" or "Pinhole Gum Rejuvenation." Newly developed instruments are inserted through a pinhole incision high above the tooth. The dentist then loosens the gum, pulling it down to cover the exposed area. Collagen is added to stabilize the gum over the teeth while it heals. No grafting is needed, and there are no stitches because the pinhole incision heals on its own. The procedure can usually be done with local anesthetics and with only mild painkillers needed after the procedure. Additionally, more teeth can be treated at once in a single procedure using the new procedure (i.e. four to five teeth instead of one to two teeth).

Even this new technique has limitations. The cost for the new procedure is comparable to the cost of traditional gum grafting. Where the patient's needs for treatment are more extensive, multiple visits to the dentist are still required. While success rates for the new treatment are generally high, there may still be problems with obtaining sufficient results in a timely fashion. While the new procedure uses a much smaller incision than previous procedures, an incision is still made, and accompanying risks result.

BRIEF SUMMARY OF THE INVENTION

A non-surgical treatment for receding gums utilizes the fact that tissue responds to continuous controlled mechanical forces with growth. For example, tissue expansion devices are used to generate extra soft tissue in vivo to be used in surgical reconstructions. The treatment applies a vacuum force to the receded gums and causes gradual regrowth of the gums to a desired extent.

An implementation of the treatment system includes a treatment impression (or appliance) (a negative mold of hard and soft tissues of the mouth) of the upper and/or lower teeth, including the surrounding existing gums, so that a vacuum can be established within the impression around teeth and gums. Before use, selected portions of the impression are carved out or otherwise formed a desired amount to create a location for the expansion and regrowth of the gums. Additionally, one or more channels may be included in the impression for delivery of the vacuum to all areas encompassed by the impression. The treatment system also includes a vacuum source operatively attached to the impression so as to be able to deliver a vacuum to the impression once the impression is place in the patient's mouth over the teeth and gums.

An alternate system still includes a treatment impression (or appliance), but the treatment impression is formed using a different process. After an initial impression is made of the teeth and surrounding existing gums, and a positive mold (or cast) is formed from the initial impression, the doctor and/or dentist determines the areas for treatment. The areas to be treated (the areas where new tissue is desired to be located) are then built up on the surface of the impression. This creates channels for growth. A form fitting treatment impression or appliance is then produced by being formed using existing methods (e.g. vacuum-formed) over the dental mold or cast. Areas built up on the mold or cast then become relief areas in the appliance and gum tissue can be mechanically pulled and/or regrown in desired areas and locations According to implementations of the invention, a system for non-surgical treatment of receding gums includes an impression selected from the group consisting of a) an impression of upper teeth and surrounding gums and b) an impression of lower teeth and surrounding gums, wherein the impression includes an impression of portions of teeth having receded gums, an impression of remaining gums surrounding the teeth having receded gums, and a void between the teeth having receded gums and the remaining gums, and the system includes a vacuum source operatively connected to the impression so as to be configured to deliver a vacuum force to the impression when the impression is worn over the teeth having receded gums and the remaining gums surrounding the teeth having receded gums.

The vacuum source may be operatively connected to the impression via a vacuum tube configured to extend externally from a mouth of a wearer. The vacuum source may be configured to be partially to entirely disposed within a mouth of the wearer while the impression is worn. The vacuum source may be configured to be actuated by a chewing motion of a wearer of the impression. The vacuum source may be manually operated. The vacuum source may be machine operated.

The system may also include a pressure valve operatively connected to the system and configured to prevent delivery of too strong a vacuum force to the impression. The impression may also include a vacuum channel extending along an inner surface of the impression to facilitate delivery of the vacuum force from the vacuum source to all desired portions of the impression.

According to further implementations of the invention, an impression for non-surgical treatment of receding gums includes an impression of portions of teeth having receded gums, an impression of remaining gums surrounding the teeth having receded gums, and a void between the teeth having receded gums and the remaining gums. The impression may also include a vacuum channel extending along an inner surface of the impression to facilitate delivery of the vacuum force from the vacuum source to all desired portions of the impression.

According to further implementations of the invention, a method for non-surgical treatment of receding gums includes creating an impression of portions of teeth having receded gums and remaining gums surrounding the teeth having receded gums and removing portions of the impression around the teeth having receded gums to create a void extending from a portion of the receded gums along a tooth having receded gums.

The method may also include placing the impression on the teeth having receded gums. The method may also include supplying a vacuum to the impression while the impression is on the teeth having receded gums. The vacuum may be supplied to the impression for a period of time sufficient to cause the receded gums to grow to fill the void. The vacuum may be supplied through a tube connected between the impression and a vacuum source. The vacuum source may be a vacuum source selected from the group consisting of a mechanical vacuum source and an electrical vacuum source. The vacuum may be supplied by a vacuum source disposed within the wearer's mouth. The vacuum may be supplied by a vacuum source located externally to the wearer's mouth.

The method may also include removing a portion of an inner surface of the impression to create a vacuum channel extending along the teeth having receded gums. Removing portions of the impression around the teeth having receded gums may include creating one or more voids corresponding to all locations of receded gums.

BRIEF DESCRIPTION OF THE SEVERAL VIEWS OF THE DRAWINGS

The objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described and explained with additional specificity and detail through the use of the accompanying drawings in which:

DETAILED DESCRIPTION OF THE INVENTION

A description of embodiments of the present invention will now be given with reference to the Figures. It is expected that the present invention may take many other forms and shapes, hence the following disclosure is intended to be illustrative and not limiting, and the scope of the invention should be determined by reference to the appended claims.

In the description and claims, the terms "treatment impression" and "appliance" are intended to be used interchangeably.

A non-surgical treatment for receding gums utilizes the fact that tissue responds to continuous controlled mechanical forces with growth. For example, tissue expansion devices are used to generate extra soft tissue in vivo to be used in surgical reconstructions. The treatment applies a vacuum force to the receded gums and causes gradual regrowth of the gums to a desired extent.

The treatment system includes a treatment impression (a negative mold of hard and soft tissues of the mouth) of the upper and/or lower teeth, including the surrounding existing gums, so that a vacuum can be established within the impression around teeth and gums. Before use, selected portions of the impression may be carved out or otherwise formed a desired amount to create a location for the expansion and regrowth of the gums. Additionally, one or more channels may be included in the impression for delivery of the vacuum to all areas encompassed by the impression. The treatment system also includes a vacuum source operatively attached to the impression so as to be able to deliver a vacuum to the impression once the impression is place in the patient's mouth over the teeth and gums.

According to embodiments of the invention, a system for non-surgical treatment of receding gums includes an impression selected from the group consisting of a) an impression of upper teeth and surrounding gums and b) an impression of lower teeth and surrounding gums, wherein the impression includes an impression of portions of teeth having receded gums, an impression of remaining gums surrounding the teeth having receded gums, and a void between the teeth having receded gums and the remaining gums, and the system includes a vacuum source operatively connected to the impression so as to be configured to deliver a vacuum force to the impression when the impression is worn over the teeth having receded gums and the remaining gums surrounding the teeth having receded gums.

The vacuum source may be operatively connected to the impression via a vacuum tube configured to extend externally from a mouth of a wearer. The vacuum source may be configured to be partially to entirely disposed within a mouth of the wearer while the impression is worn. The vacuum source may be configured to be actuated by a chewing motion of a wearer of the impression. The vacuum source may be manually operated. The vacuum source may be machine operated.

The system may also include a pressure valve operatively connected to the system and configured to prevent delivery of too strong a vacuum force to the impression. The impression may also include a vacuum channel extending along an inner surface of the impression to facilitate delivery of the vacuum force from the vacuum source to all desired portions of the impression.

According to further embodiments of the invention, an impression for non-surgical treatment of receding gums includes an impression of portions of teeth having receded gums, an impression of remaining gums surrounding the teeth having receded gums, and a void between the teeth having receded gums and the remaining gums. The impression may also include a vacuum channel extending along an inner surface of the impression to facilitate delivery of the vacuum force from the vacuum source to all desired portions of the impression.

According to further embodiments of the invention, a method for non-surgical treatment of receding gums includes creating an impression of portions of teeth having receded gums and remaining gums surrounding the teeth having receded gums and removing portions of the impression around the teeth having receded gums to create a void extending from a portion of the receded gums along a tooth having receded gums.

The method may also include placing the impression on the teeth having receded gums. The method may also include supplying a vacuum to the impression while the impression is on the teeth having receded gums. The vacuum may be supplied to the impression for a period of time sufficient to cause the receded gums to grow to fill the void. The vacuum may be supplied through a tube connected between the impression and a vacuum source. The vacuum source may be a vacuum source selected from the group consisting of a mechanical vacuum source and an electrical vacuum source. The vacuum may be supplied by a vacuum source disposed within the wearer's mouth. The vacuum may be supplied by a vacuum source located externally to the wearer's mouth.

The method may also include removing a portion of an inner surface of the impression to create a vacuum channel extending along the teeth having receded gums. Removing portions of the impression around the teeth having receded gums may include creating one or more voids corresponding to all locations of receded gums.

Figure 1:
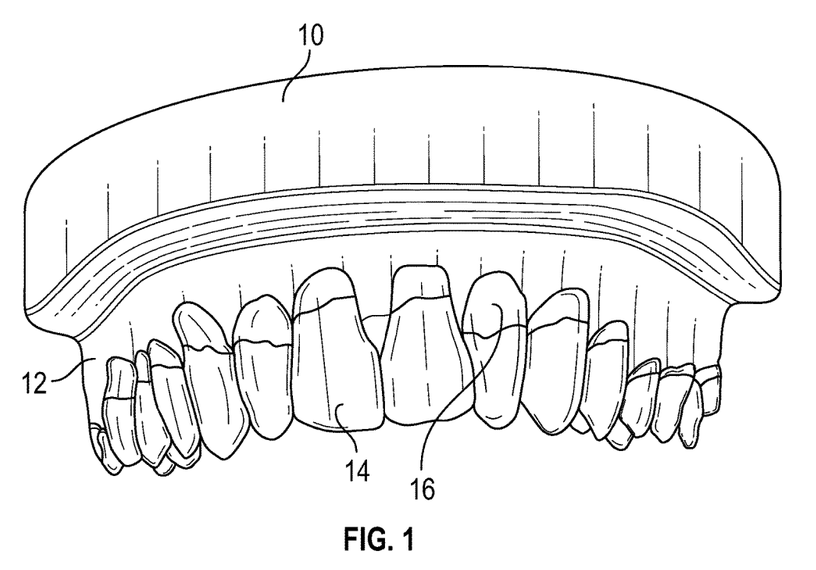
FIG. 1 shows a representative jaw with receded gums.
Figure 2:
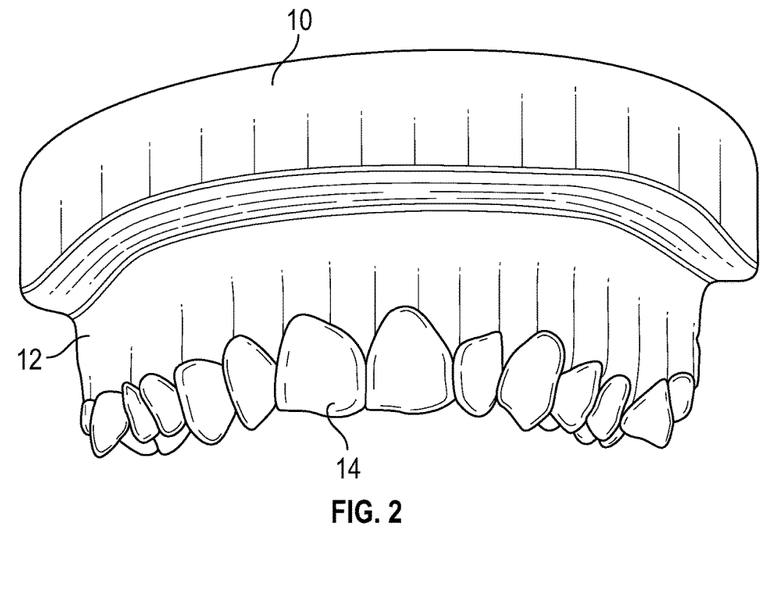
FIG. 2 shows a representative jaw with desired gums.

To assist in understanding the various implementations of the invention, FIG. 1 illustrates (in isolation) a jaw 10 having receded gums 12. The receded gums 12 have exposed portions of teeth 14 having receded gums 12 that should normally be covered by gums 12, namely roots 16. The amount of root 16 exposed on each tooth 14 may vary from tooth to tooth in each patient, but patients commonly have a problem on multiple teeth. In contrast, FIG. 2 illustrates a similar jaw 10 having normal gums 12 that cover the roots 16 of the teeth 14. The goal of treatment of the example of FIG. 1 may be to achieve the results of FIG. 2.

To treat the receding gums of FIG. 1, a dentist takes an initial impression (which is a negative mold) of the jaw 10, including at least the teeth 14 having receded gums 12 and the gums 12 surrounding the teeth 14 having receded gums 12. The initial impression should include the surrounding gums 12 so as to provide a location to which a treatment impression can contact while being worn to maintain a vacuum within the treatment impression. The initial impression may be made using techniques known in the dental art. The initial impression is then used to create a positive mold of the wearer's jaw 10, which in many instances also greatly resembles the view of FIG. 1, except that the soft tissues of the gums 12 and the various individual teeth 14 are replaced by a unitary hard material such as plaster. Again, the creation of the positive mold may be done using methods known in the art.

In one example, the positive mold is then used to create a treatment impression (negative mold) of the teeth 14 and surrounding gums 12, again using methods known in the dental art, such as methods used for creating retainers and mouth guards. The treatment impression may be made of a variety of materials such as those known in the dental art, and will typically have sufficient flexibility to be comfortable to wear while having sufficient rigidity so as not to collapse or overly flex when exposed to a mild vacuum force as discussed below. In some embodiments, the treatment impression may be formed of multiple materials: a more-rigid material may be located so as to contact the teeth and to define the area of receded gums, while a less-rigid, softer, or more comfortable material may be located so as to contact the surrounding gums for increased comfort of the wearer of the device. The treatment impression is verified to completely surround the teeth 14 of interest and to contact the receded gums 12 surrounding all the teeth 14 of interest, so that a vacuum can readily be maintained.

At this stage, the treatment impression follows the receded gums 12 of FIG. 1. The next step in the treatment is to remove portions of the material of the treatment impression corresponding to the locations where gum 12 growth is desired. These are locations extending along the teeth 14 having receded gums 12 from the current location of the receded gums 12. As the material is removed, it provides a location for the vacuum to draw the receded gums 12 into, and for the receded gums 12 to grow into in response to the vacuum force.

Figure 3:
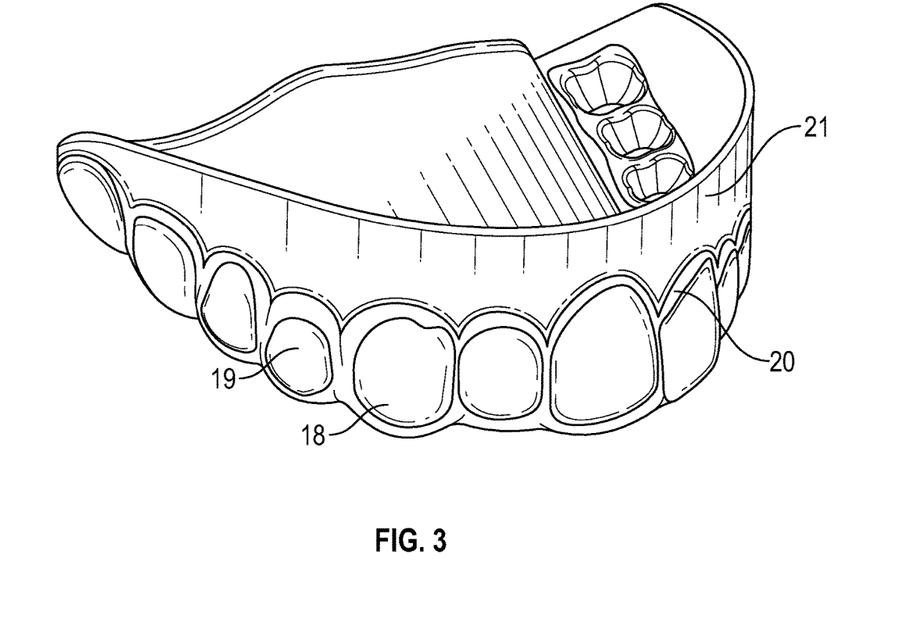
FIG. 3 shows a representative treatment impression or appliance.

Once the material is removed, a positive mold created from the treatment impression might resemble what is shown in FIG. 2. In such an example, only enough material is removed to exactly resemble the desired final result. Alternatively, because it may be desirable to remove additional material to permit some relaxation of the gums 12 after treatment, it should be recognized that some additional material may be removed such that a resultant positive mold created from the treatment impression would appear to have swollen and larger gums than the desired final result. FIG. 3 shows an example of a treatment impression 18, and shows a tooth-contacting portion 19, a void 20 created in the treatment impression 18 into which the receded gums will be drawn, and a gum-contacting portion 21. The tooth-contacting portion 19 conforms to portions of teeth having receded gums, and the gums-contacting portion 21 conforms to remaining portions of the receded gums.

Figure 4:
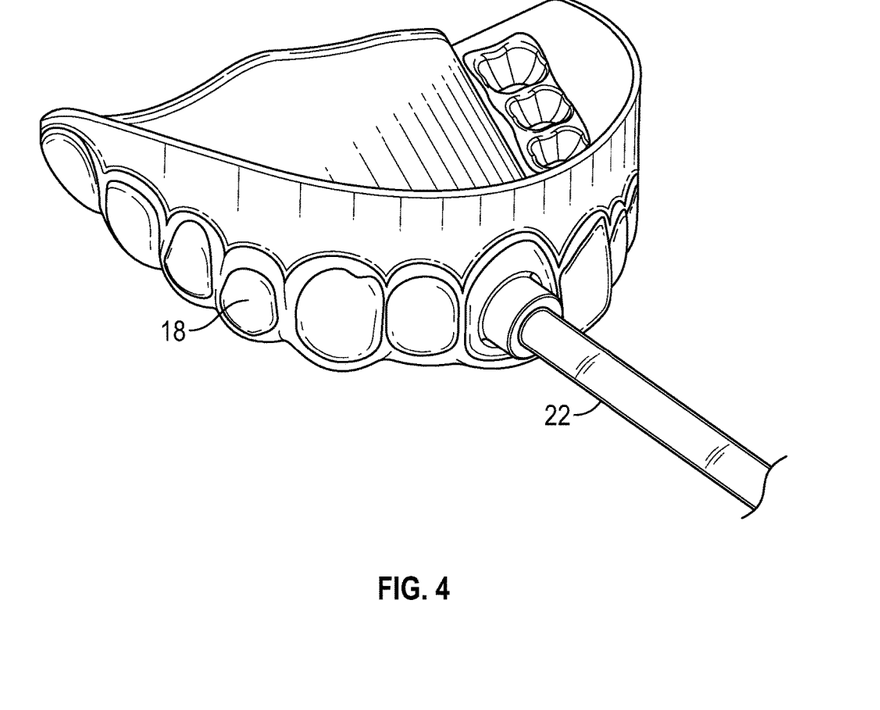
FIG. 4 shows a representative treatment impression or appliance with a suction tube extending therefrom.

In some instances, additional material of the treatment impression may be removed to create a vacuum channel, or the void 20 may serve as the vacuum channel. Although the vacuum will commonly reach all areas of interest without requiring a vacuum channel, a vacuum channel will allow a vacuum to be more quickly and evenly established within the treatment impression. The treatment impression is modified to be connected to a vacuum source (such as by creating a hole through the treatment impression at a single point to which a vacuum tube 22 is attached, as illustrated in FIG. 4). Optionally, a pressure relief valve may be incorporated into the treatment impression to prevent over-application of vacuum to the treatment impression, or the pressure relief valve may be located at the vacuum source or anywhere between the vacuum source and the treatment impression. Finally, the treatment impression is checked by insertion into the mouth of the patient to verify proper fit and comfort.

An alternate method for creating the treatment impression involves a similar removal of material from the initial impression. The result will be that the positive mold will have additional material where the material was removed from the initial impression. Then, when the treatment impression is formed, the additional material on the positive mold will cause a similar gap to be formed between the impression and the user's teeth. Because this alternate method is in some ways destructive of the original initial impression and is not tolerant of mistakes, it is envisioned that this method, while equally effective if performed correctly, will not often be used in practice.

Figure 5:
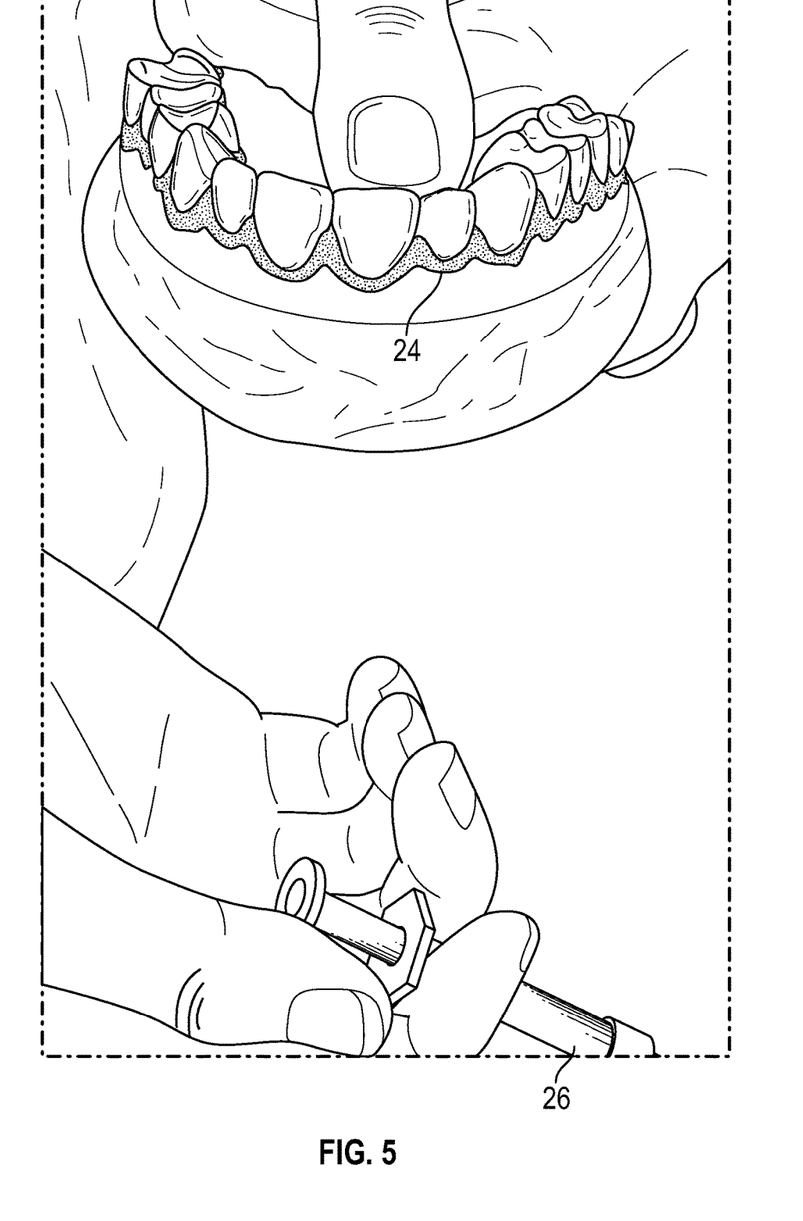
FIG. 5 shows a representative positive mold or cast with material added thereto.
Figure 6:
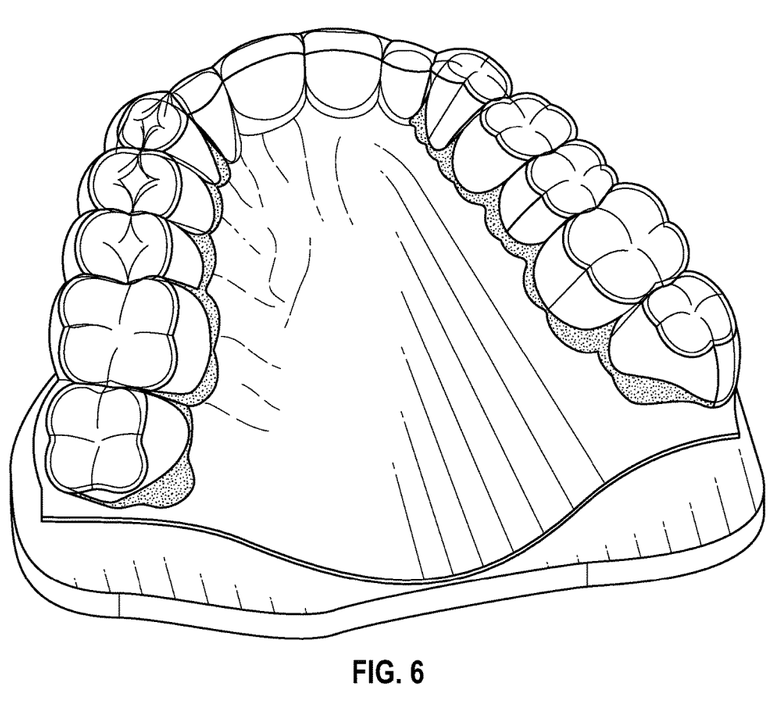
FIG. 6 shows a representative treatment impression or appliance formed on the representative positive mold.
Figure 7:
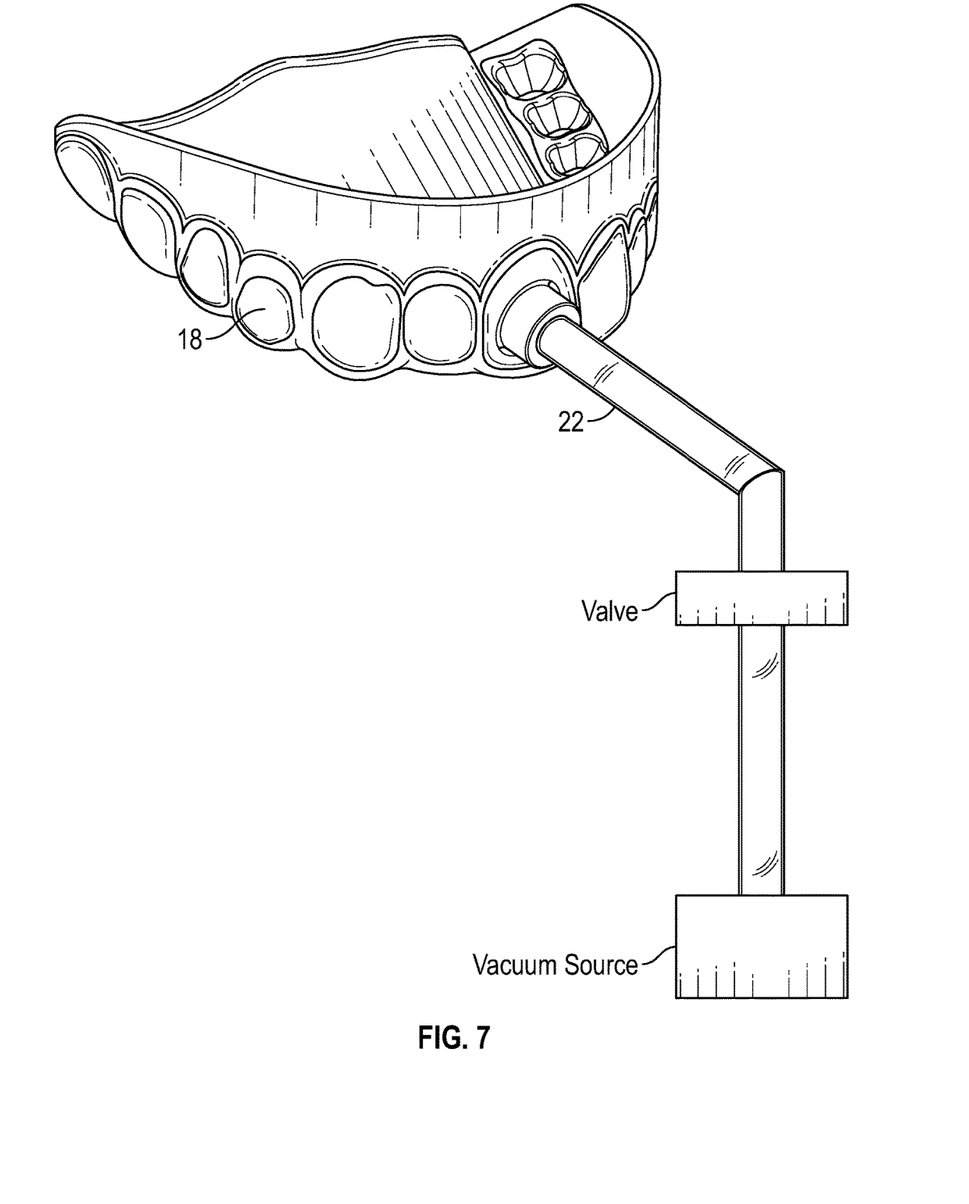
FIG. 7 shows a representative treatment impression or appliance with a suction tube extending therefrom to a vacuum source through a pressure valve.

A still alternate method for creating the treatment impression involves modification of the positive mold. This process is illustrated in FIGS. 5-6, and results in a similar finished product as was illustrated in FIGS. 3-4. In this process, the initial impression and positive mold are created as previously discussed. Before the treatment impression is created, however, material 24 defining the void into which the receding gums are to be drawn by the mild vacuum is added to the positive mold. This addition of material 24 is illustrated in FIG. 5. As is illustrated in FIG. 5, the material 24 may be added using a syringe 26 or other dispenser, and the material 24 may be colored differently or textured differently from the positive mold so that the practitioner can readily see or envision the gum growth to be achieved and the correction to be made to the receded gums. The material 24 may be a material that will essentially permanently bond to the positive mold, or it may be a material that can be removed or reshaped as desired.

The difference in coloring or texturing of the material 24, in addition to helping the practitioner see or envision the extent of gum regrowth to be achieved, also aids the practitioner during the step of forming the treatment impression, as the practitioner ensures that the treatment impression extends on all sides past the void defined by the addition of the material 24 to contact the remaining gums. This is illustrated in FIG. 6, which shows the treatment impression just after it has been formed on the modified positive mold using traditional methods of the dental art, as discussed above. While not illustrated in FIGS. 5 and 6, the material 24 may also be added to the positive mold prior to forming the treatment impression to define a vacuum channel along the teeth (or the vacuum channel may be formed by a removal process as discussed above). The remaining steps in the process proceed as discussed above.

Regardless of the method by which the treatment impression is created, the treatment impression is then used to treat receding gums as follows. A vacuum (or suction) source is connected to the treatment impression. The vacuum or suction source may be any such source capable of delivering a vacuum to the treatment impression. The vacuum source may be an electrically driven source, or it may be mechanically driven. It may be automatically or manually operated. The vacuum source may be one configured to be disposed within the mouth of the wearer of the treatment impression (such as a vacuum source configured to be actuated by a biting motion of the wearer), or it may be configured to be disposed externally to the mouth of the wearer and connected to the treatment impression via a vacuum tube. Alternatively, the wearer may create sufficient suction within the device simply by sucking on the device after placement.

The wearer places the treatment impression in the mouth so that the edges of the treatment impression contact the gums 12 surrounding the teeth 14 having receded gums 14. Then, the vacuum source is actuated to supply a vacuum to the impression. The vacuum need not be exceptionally strong, but it will gently pull the gums 12 surrounding the teeth 14 having receded gums into the void(s) surrounding the teeth 14 having receded gums 12 created by the removal of material discussed above. The treatment time may vary according to the severity of the receded gums and the desired amount of tissue regrowth, but it is anticipated that daily treatments of as many as ten hours of treatment may occur over a period of weeks to months. Over this time, the stretching of the gums by the vacuum source will cause the gums to initially swell, but to over time respond with vascularized healthy tissue growth which will eventually restore a normal gum appearance and function as shown in FIG. 2.

The treatment discussed herein need not be limited to addressing severe receded gums. In fact, the treatment discussed herein may also be used in preventive fashion, including from time to time to maintain treatment gains from past treatment. Furthermore, the suction generated by the system may have other benefits yet to be fully explored, such as a reduction/suction/extraction of bacteria beneath the gum line.

The present invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed and desired to be secured by Letters Patent is:

1. A system for non-surgical treatment of receding gums, comprising:
    a dental impression selected from the group consisting of
        a) an impression of upper teeth and surrounding gums and b) an impression of lower teeth and surrounding gums, wherein the dental impression comprises:
        a tooth impression portion conforming to portions of teeth having receded gums;
        a gum impression portion conforming to portions of remaining gums surrounding the teeth having receded gums; and
        a void portion configured to define a void extending along the teeth having receded gums and defining an area into which growth of the remaining gums is desired;
    wherein the dental impression further comprises a vacuum channel extending along an inner surface off the dental impression to facilitate delivery of a vacuum force from a vacuum source to the void portion of the dental impression.

2. The system as recited in claim 1, further comprising a vacuum source operatively connected to the dental impression so as to be configured to deliver a vacuum force to the dental impression when the dental impression is worn over the teeth having receded gums and the remaining gums surrounding the teeth having receded gums.

3. The system as recited in claim 1, wherein the system further comprises a pressure valve operatively connected to the system and configured to prevent delivery of a vacuum force exceeding a selected vacuum force to the dental impression.

4. The system as recited in claim 1, wherein the dental impression further comprises a material positioned on the gum impression portion that is less rigid than a material positioned on the tooth impression portion.

5. A dental impression for non-surgical treatment of receding gums comprising:
- a tooth impression portion conforming to portions of teeth having receded gums;
- a gum impression portion conforming to portions of remaining gums surrounding the teeth having receded gums;
- a void portion configured to define a void extending along the teeth having receded gums and defining an area into which growth of the remaining gums is desired; and
- a vacuum channel extending along an inner surface off the dental impression to facilitate delivery of a vacuum force from a vacuum source to the void portion of the dental impression.

6. The dental impression as recited in claim 5, wherein the dental impression comprises a more rigid material positioned to contact the teeth and defining the void, and a less rigid, softer material positioned to contact the remaining gums.

* * * * *